United States Patent [19]

Tsuji et al.

[11] Patent Number: 4,636,196
[45] Date of Patent: Jan. 13, 1987

[54] METHOD FOR PROVIDING A BUBBLELESS CONNECTION BETWEEN FILLING TUBES FOR BLOOD OR THE LIKE AND A CONTAINER USED FOR SAID CONNECTION

[75] Inventors: Takashi Tsuji, Fujisawa; Shozo Kobayashi, Kawasaki; Toshio Nagase, Tsukuba, all of Japan

[73] Assignee: Nippon Zeon Co., Ltd., Tokyo, Japan

[21] Appl. No.: 562,697

[22] Filed: Dec. 19, 1983

[30] Foreign Application Priority Data

Dec. 27, 1982 [JP] Japan ................................. 57-226936

[51] Int. Cl.[4] .............................................. A61M 5/00
[52] U.S. Cl. .................................... 604/122; 604/905; 604/49; 137/171
[58] Field of Search .................... 604/29, 49, 122–125, 604/905; 137/171; 285/19, 20

[56] References Cited

U.S. PATENT DOCUMENTS 3,833,013  9/1974  Leonard .............................. 604/122
4,209,013  6/1980  Alexander et al. ................... 604/29
4,353,367 10/1982  Hunter ................................ 604/905

Primary Examiner—Dalton L. Truluck
Assistant Examiner—Karen L. Kaechele
Attorney, Agent, or Firm—Weingarten, Schurgin, Gagnebin & Hayes

[57] ABSTRACT

A connecting method and a container wherein a connecting tube of a blood pump or humor circulating circuit is connected to a tube such as a cannula mounted on a circulatory system organ in such a way that no bubbles enter the tubes, in order to pour blood or humor substitution fluid into the circulatory system organ.

6 Claims, 8 Drawing Figures

METHOD FOR PROVIDING A BUBBLELESS CONNECTION BETWEEN FILLING TUBES FOR BLOOD OR THE LIKE AND A CONTAINER USED FOR SAID CONNECTION

BACKGROUND OF THE INVENTION

When a connecting tube of a blood pump or a humor circulating circuit and a tube such as a cannula mounted on a circulatory system organ are connected in order to pour blood or humor substitution fluid in the circulatory system organ, it is necessary to carefully connect the tubes so as not to allow bubbles to remain within the tubes. If the bubbles are contained in blood, a blockade of blood capillaries or the like occurs, resulting in an extremely dangerous condition for a living body.

As one means for connecting two tubes filled with blood or the like to eliminate bubbles therein, there is a method for connecting the tubes while pouring the humor substitution fluid or physiological saline solution to connected ends of two tubes. In accordance with this method, a tube such as a cannula mounted on a blood vessel is supported with a connected end directed upwardly, blood is moved up to the interior of the tube by blood pressure, and thereafter, the tube is clamped below a liquid level of blood. Then, the humor substitution fluid is filled from the clamped portion to the upper connected end, and the tube is sufficiently commoved to completely discharge bubbles adhered to tube walls from the interior of the tube. Similarly, the connecting tube of the blood pump is also filled with the humor substituion fluid to completely discharge bubbles, two tubes are made to come closer to each other with connected ends thereof directed upwardly, and the connected end of one tube is inserted into the connected end of the other tube within the flowing-down humor substitution fluid while a large quantity of the humor substitution fluid to said portions which are formed to come closer to each other to connect two tubes.

In the above-described connecting method, even if bubbles are carefully discharged by commotion, air tends to be entrained into liquids since connecting of tubes is carried out within the flowing-down liquid and a part of the air is drawn into the tubes and formed into bubbles. Thus, there was a disadvantage in that the bubbles remain within the tubes despite the fact that connecting of tubes was carried out with effort.

In view of the foregoing, a connecting method has been used in which a connecting tube provided with branch tubes is used to connect two tubes, and bubbles within the tubes after connection are guided into the branch tubes for discharge. In this method, a cannula from which bubbles within the liquid have been discharged and a connecting tube are connected by insertion with the branch tubes directed upwardly, the connecting tube is curved in the form of a mountain to bring the branch tubes to the highest position, the two connected tubes are commoved to upwardly move the bubbles up to the branch tubes to completely remove the bubbles within the connected tubes, and thereafter, root portions of the branch tubes are clamped.

This method making use of the branch tubes carries out the discharge of bubbles after the tubes have been connected and therefore can positively prevent the bubbles from being retained as compared with the method of connecting tubes after removal of bubbles. However, vestiges remain on side walls of portions where the branch tubes were present and thrombus tends to occur on said vestiges. Therefore, there involves a disadvantage that in case of transfusion of blood, heparin has to be contained in blood.

As the result of a series of studies on means and apparatus for connecting two tubes which can positively remove bubbles within the tubes and which can prevent re-generation of bubbles when the tubes are connected and remain on vestiges on side walls of the tubes connected, the present inventors have found that a method can be used in which two tubes are connected within the liquid in order to facilitate connection of the tubes with bubbles being eliminated completely and positively.

SUMMARY OF THE INVENTION

It is therefore an object of the present invention to provide a new connecting method which removes the disadvantages with respect to the prior art connecting methods by accomplishment of the connection within a humor substitution fluid, for example, physiological saline solution.

The above-described object of the present invention can be achieved by connecting two tubes within a small container made of a high molecular weight substance which has flexibility and elasticity, which can be deformed wholly or partly and which further has a self-standing property. That is, the aforesaid object can be achieved by liquid-tightly inserting ends of two tubes into a container while extending through opposed side walls thereof, filling the container with humor substitution fluid, upwardly directing connected ends of two tubes within said container by deformation of a container body, commoving both the tubes and thereafter connecting them within the liquid.

The humor substitution fluid within the container body is in the static condition, and even if a liquid surface is moved up and down as the container body deforms and even if a dynamic change should occur by commotion of two tubes, there is no fear of engulfing air as in a flowing-down liquid. Furthermore, there is no fear that bubbles discharged outside the tubes by commotion are again taken into the tubes by the dynamic change of the humor substitution fluid within the container body.

In accordance with the method of the present invention, filling of humor substitution fluid into the ends of two tubes and discharging bubbles can be continuously accomplished by utilization of a deformable container. Further, tube end connecting thereby can be made under said conditions. The continuity of such connecting makes it possible to achieve a connection in a short period of time while previously requiring a long period of time, as a consequence of which preparation time for operation or the like can be shortened. The present method which can be performed without using a special technique, and positively and without fear of thrombus, is superior to the conventional method which discharges bubbles by making use of branch tubes.

It is a second object of the present invention to provide a container which can perform, by hands and continuously, filling of humor substitution fluid into two tubes, discharging of bubbles from the tubes, and connecting the two tubes.

The container that may achieve the above-described object preferably is flexible and elastic, wholly or partly deformable, transparent, and is capable of self-standing.

The container in accordance with the present invention can be formed of a soft and elastic high molecular weight substance having a transparency, for example, such as polyethylene, polyvinylchloride, ethylene-vinylacetate copolymer, silicone rubber etc. In this case, a plasticizer in polyvinylchloride resin can be used, for example, dioctylphthalate, dioctyladipate etc. Said plastics have 40-100 weight parts for 100 weight parts of polyvinylchloride, preferably, 50-80 weight parts. Vinylacetate in ethylene-vinylacetate copolymer is preferably 5-20 weight parts.

The aforementioned container preferably has a plurality of through-holes into which two tubes to be connected are inserted, flanges for liquid-tightly holding the tubes around said through-holes irrespective of their angle of intersection, and skirts for facilitating insertion of the tubes.

The through-holes are so bored as to fit closely an inserting portion of a tube thereinto. The diameter of the through-holes is made smaller than an outside diameter of the inserting portion of the tube to be inserted, preferably about 70-95%.

The present invention will be described in detail hereinafter by way of the illustrated embodiments.

DESCRIPTION OF THE PREFERRED EMBODIMENTS

Figure 1:
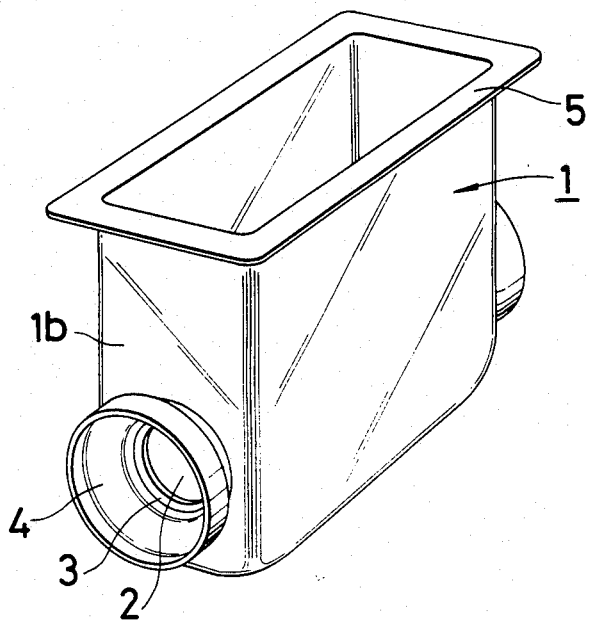
FIG. 1 is a perspective view of a container which is used for a connecting method in accordance with the present invention.
Figure 2:
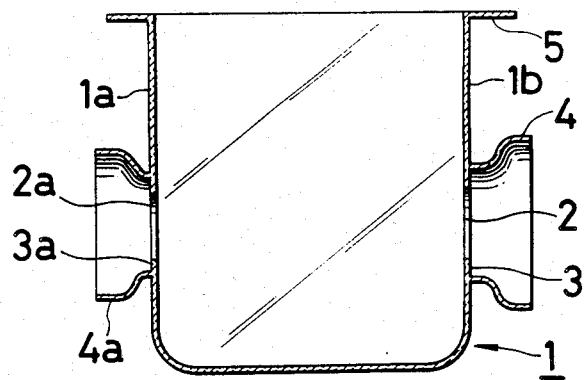
FIG. 2 is a lontitudinal front view of said container.

In the drawings, a reference numeral 1 designates a container formed of polyvinylchloride with an upper portion thereof open, which has flexibility and elasticity and which is deformable wholly or partly but has a self-standing property. The container 1 is rectangular in plane shape, has dimensions of longitudinal sides about 60 mm, lateral sides about 30 mm and a depth about 70 mm, and is formed by a thin wall container body which has a wall-thickness about 1 mm, is transparent and has a deep bottom.

Opposed walls 1a, 1b positioned lengthwise of the container body are bored to form through-holes 2, 2a through which tubes are preferably inserted at the same postition, and flanges 3, 3a are provided around the through-holes 2, 2a. Cup-like skirts 4, 4a encircling the through-holes 2, 2a and flanges 3, 3a are provided that project therefrom like ears integral with the outer surfaces of the opposed side walls 1a, 1b, and a flange portion 5 is formed integral with an open peripheral edge of the container body. The container 1 can be held by fingers so that the container may be bended freely, and the opposed side walls 1a, 1b can be pressed inwardly to make the through-holes 2, 2a closer to each other.

The diameter of the through-holes 2, 2a is 80% smaller than the outside diameter of the inserting portion of the blood filling tube to be inserted thereinto to insure that the tube to be inserted may be water-tightly fixed, and even when the container body is deformed, the closely fitting property of the tubes relative to the side walls of the container may be maintained. The skirts 4, 4a are provided to serve as pulling ears when the tube is inserted into the through-holes 2, 2a while spreading the latter and are extremely effective when the tube is inserted. The flange portion 5 is provided to prevent free deformation of the soft container, to hold the container generally in the form of a box and to prevent the container from overflowing of the humor substitution fluid. Furthermore, since the flange portion 5 is not greatly deformed when the container is deformed by pressing or the like, the flange portion is convenient for carrying out the procedures wherein the humor sustitution fluid is filled, after which tubes are connected within the liquid, as will be described later.

Portions corresponding to ridges and apexes of a box of the container 1 are all formed to have a gently-sloping curved surface to prevent bubbles from being retained within the container body, particularly, in said portions. The container 1 is made to be transparent so as to easily check residual bubbles within the container and to connect tubes.

Figure 3:
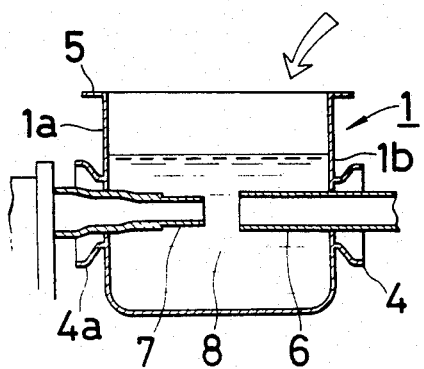
FIGS. 3 to 6 are longitudinal front views of the container and two tubes showing the preferred order of the connecting steps of the present invention.

Next, the method of the present invention will be explained by way of an example in which the aforementioned container 1 is used to connect an end of a cannula mounted on a blood vessel with a connecting tube mounted on a blood pump. Blood is moved up in advance within the cannula to extrude air therein, the cannula is clamped below the liquid level, humor substitution fluid is filled from a calmp portion to the end of the cannula, the end 6 of the cannula is forced into the tube inserting through-hole 2 of the container 1, and at the same time, the tube is inserted through the through-hole 2 while pulling the skirts 4. The diameter of the through-hole is 80% smaller than the outside diameter of the cannula, and the tube can be closely fitted therein with the aid of the flexibility and elasticity of the flange portion 3. Similarly, the tube 7 of the blood pump filled with the humor substitution fluid to the tube end of the other tube is inserted into the through-hole 2a, and the humor substitution fluid is poured into the container as shown in FIG. 3.

Figure 4:
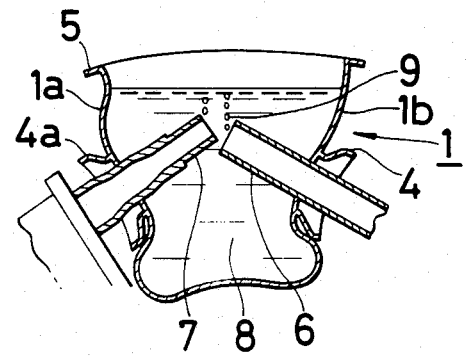
Figure 5:
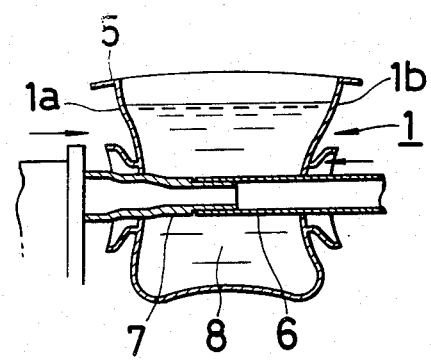
Figure 6:
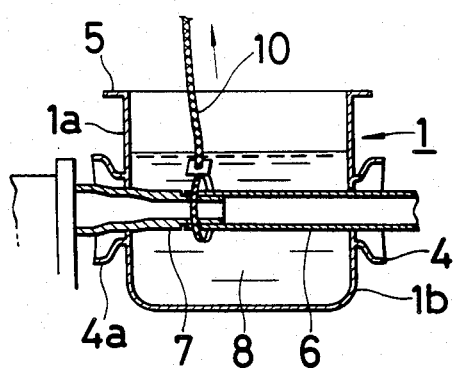

Next, as shown in FIG. 4, the respective tube ends are upwardly inclined below the liquid level of the container, and the tubes are commoved to completely expel bubbles adhered to and retained in the tubes, after which both side walls of the container are pressed to connect the tube ends below the liquid level, as shown in FIG. 5. Next, as shown in FIG. 6, the connected portions of the tubes are fastened, for example, by a tie band 10 using a foceps or the like below the liquid level of the container to absolutely prevent the connected portions from being disengaged. In accordance with this method, there occurs no entry of bubbles into the connected tube ends resulting from looseness of the connected portions, unlike the case of prior art where the connected portions are fixed by a tie band in air. The blood pump is actuated under the condition that the connected portions are immersed into the liquid in the container to check presence of a leakage of the liquid at the connected portions, and if any trouble occurs, such trouble can be remedied by hand. Thus, this method is extremely safe.

After the tubes have been connected, the container can be torn off and removed because the container is an obstacle to the operation which will be made later. Alternatively, the container can be designed with a tearing-off shallow groove line so that the container may readily be torn off.

Figure 7:
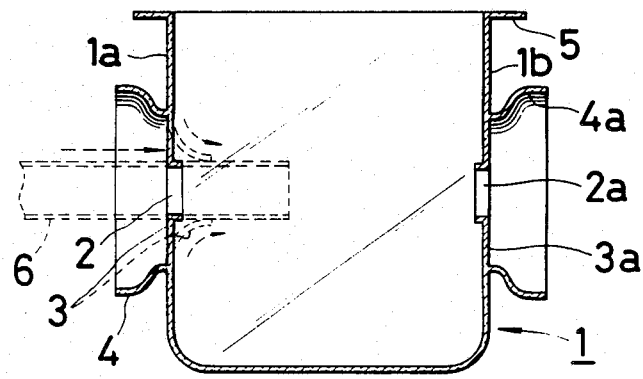
FIG. 7 is a longitudinal front view showing a further embodiment of the container.

The container used for the method of the present invention is not limited to the type as described above but, for example, the side wall portions formed with the through-holes 2, 2a can be given such flexibility and elasticity that they may be deformed, or as shown in FIG. 7, the flange portions 3, 3a around the through-holes 2, 2a can be formed of a stretchable material having flexibility and elasticity such as rubber elasticity.

Figure 8:
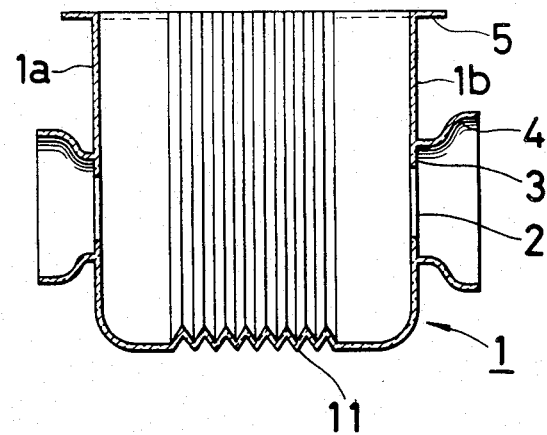
FIG. 8 is a longitudinal front view showing a still another embodiment of the container.

Also, a bellows portion 11 may be provided on a body of the container, as shown in FIG. 8, so that it may be bended and expanded. Furthermore, a closed type in which an upper portion of a flange is closed can be employed and one or two tubes for pouring fluid are mounted on the ceiling portion. The shape of the container is not limited to the box-shape but suitable shapes such as cylindrical and elliptical shapes in section can be selected. In short, the container used must only have a size in which a tube can be inserted through side walls and operated below the liquid level in the container, and have a design so that the wall portions of the container are soft, have an elasticity and are deformable.

What is claimed is:

1. A container for connecting filling tubes for blood or the like, comprising:
    a container body having an upper opened-portion defining a fluid receiving interior chamber and an external surface;
    said container body being formed of a high molecular weight substance that is flexible, elastic, and wholly or partly deformable;
    said container body having opposed confronting sidewalls;
    each of said opposed confronting sidewalls of said container body having a through-hole of a predetermined dimension through which the end of each of two tubes to be connected are respectively insertable into said container body;
    a skirt formed with each of said opposed sidewalls and outwardly projecting from said external surface of said container body defining a flange-like appurtenance surrounding an associated one of said tube insertable through-holes; and
    a flange integrally formed along the periphery of said opened-portion of said container body for strengthening said container body.

2. A connecting container according to claim 1, wherein said container body, said skirts, and said flange are integrally formed of such high molecular weight substances as polyvinylchlorides, polyethylene, ethylene-vinylacetate copolymer, and silicone rubber.

3. A connecting container according to claim 1, wherein said skirts are formed concentrically with said through-holes and in the form of a laterally outwardly projecting cup.

4. A connecting container according to claim 1, wherein said through-holes are formed smaller than the outside diameter of an inserting portion of a corresponding one of said tubes to be inserted.

5. A connecting container according to claim 4, wherein said diameters of said through-holes are 70-95% smaller than the outside diameter of a corresponding one of said tubes to be inserted.

6. A method for connecting filling tubes for blood or the like, wherein a tube such as the connecting tube of a blood pump or humor circulating circuit is connected to a tube such as a cannula mounted on a circulatory system organ in such a way that bubbles are effectively removed from the tubes, comprising the steps of:
    using a container having a top and formed of a high molecular weight substance which has flexibility, elasticity, and which is deformable wholly or in part;
    inserting the ends of said tubes into said container in such a way that each extends through an opposed side wall of the container and with their ends in spaced-apart confronting relation;
    filing the container with a liquid to such a level therein that the ends of said tubes are below the level of the liquid in the container and in fluid communication therewith;
    angling the inserted ends of the spaced-apart tubes while immersed in the liquid so as to face towards the top of the container;
    commoving said container and inserted tubes while the tube ends are submerged within the liquid and angled toward the top so as to induce any bubbles present within the tubes to be moved out of the ends of the tube and raise through the liquid; and
    collapsing said container into itself so as to connect the open ends of said tubes together while said tube ends are still submerged within said liquid.

* * * * *